United States Patent
Cooray et al.

(10) Patent No.: US 7,597,980 B2
(45) Date of Patent: Oct. 6, 2009

(54) SULFONIC ACID GROUP-CONTAINING, PROTON-CONDUCTING POLYMER COMPOSITION, A SOLID ELECTROLYTE MEMBRANE AND A SOLID POLYMER FUEL CELL

(75) Inventors: Nawalage Florence Cooray, Kawasaki (JP); Fumio Takei, Kawasaki (JP); Norio Sawatari, Kawasaki (JP); Masao Tomoi, Yokohama (JP)

(73) Assignee: Fujitsu Limited, Kawasaki (JP)

( * ) Notice: Subject to any disclaimer, the term of this patent is extended or adjusted under 35 U.S.C. 154(b) by 883 days.

(21) Appl. No.: 11/081,077

(22) Filed: Mar. 16, 2005

(65) Prior Publication Data

US 2005/0221135 A1    Oct. 6, 2005

(30) Foreign Application Priority Data

Mar. 30, 2004 (JP) ............................. 2004-097398

(51) Int. Cl.
*H01M 8/10* (2006.01)
*H01M 8/18* (2006.01)
*C08G 73/06* (2006.01)

(52) U.S. Cl. .................. 429/33; 429/12; 429/30; 528/171; 528/391; 521/27

(58) Field of Classification Search .............. 521/27; 528/391, 171; 429/30, 12, 33
See application file for complete search history.

(56) References Cited

FOREIGN PATENT DOCUMENTS

| JP | 2001-354641 | 12/2001 |
|---|---|---|
| JP | 2002-3466 | 1/2002 |
| JP | 2003-22709 | 1/2003 |
| JP | 2003-335835 | 11/2003 |
| JP | 2005-133092 A | 5/2005 |

OTHER PUBLICATIONS

Japanese Office Action dated Jun. 17, 2009, issued in corresponding Japanese Application No. 2004-097398.

*Primary Examiner*—Duc Truong
(74) *Attorney, Agent, or Firm*—Westerman, Hattori, Daniels & Adrian, LLP.

(57) ABSTRACT

A solid electrolyte membrane for solid polymer fuel cells, or the like is provided that is chemically stable in a strong acid atmosphere, and has low methanol cross-over as well as high proton conductivity. The solid electrolyte membrane is manufactured, using an electrolyte composition comprising a sulfonic acid group-containing polymer having a specific triazine structure. This polymer can be synthesized, for example, from a sulfonic acid group-containing dihydroxy compound having a triazine structure, and a difluoride.

26 Claims, 12 Drawing Sheets

$Ar^1$ (n=1~4)

$Ar^2$ (n=1~4)

FIG. 1
Ar¹ 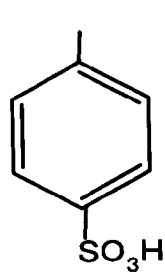 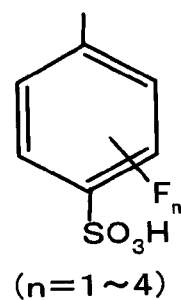 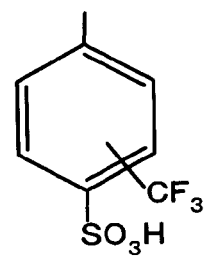
(n=1~4)
Ar²  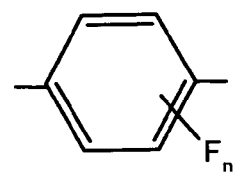
(n=1~4)

FIG. 2 Ar³
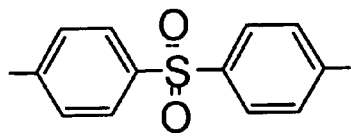
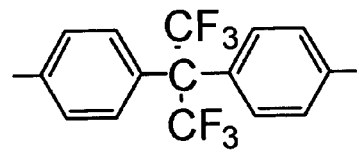
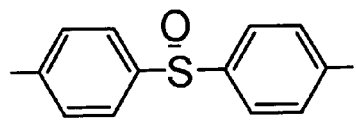
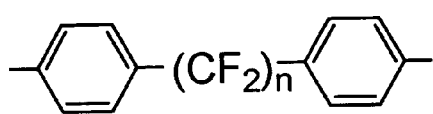
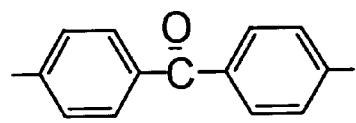
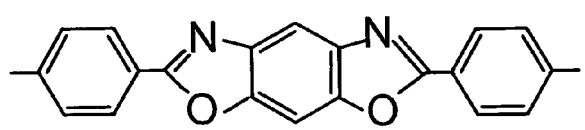
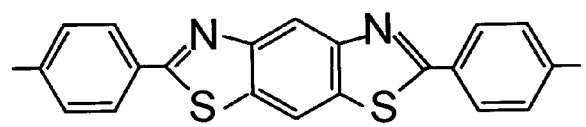
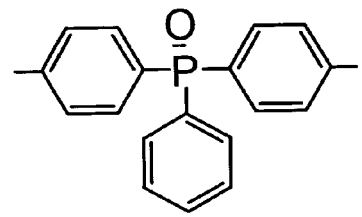
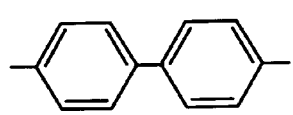
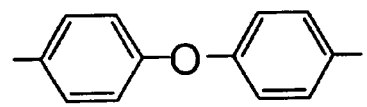
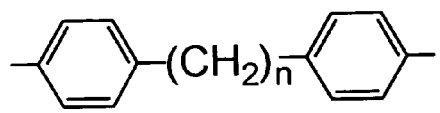
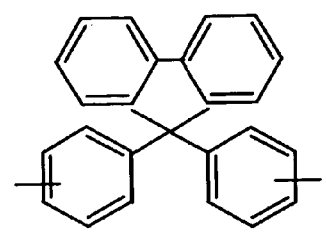
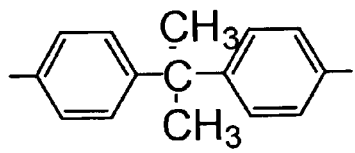

FIG. 3 Ar⁴
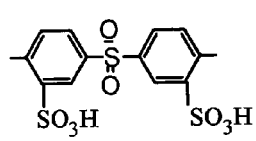
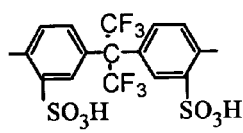
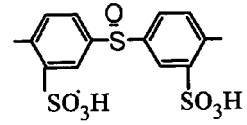
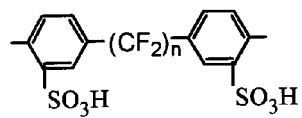
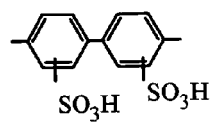
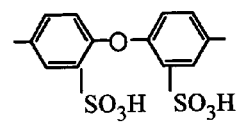
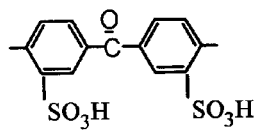
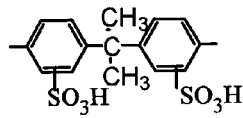
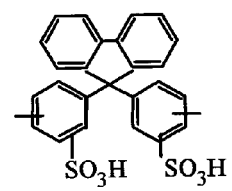
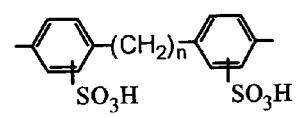

FIG. 4
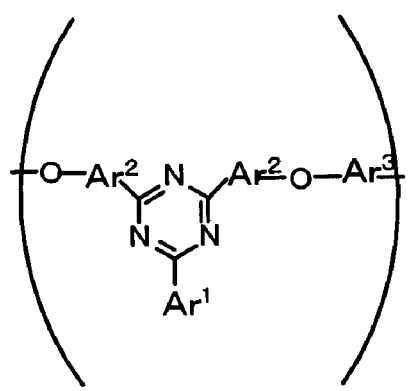
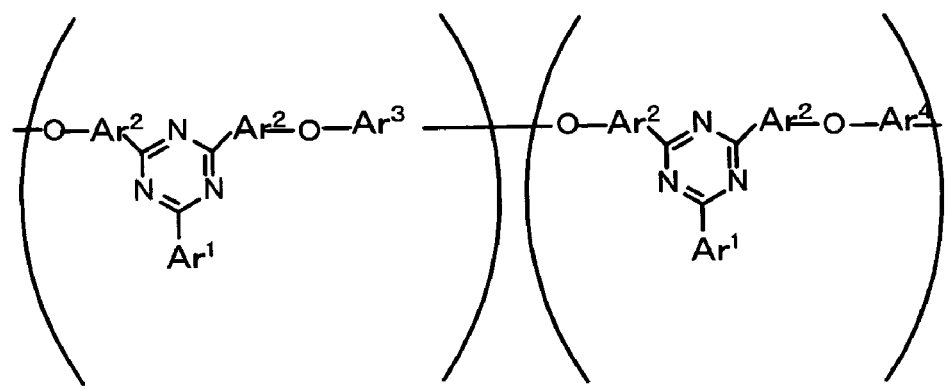

FIG. 13
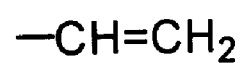  
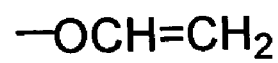  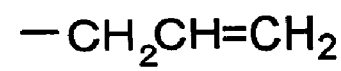
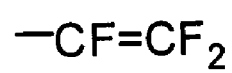  
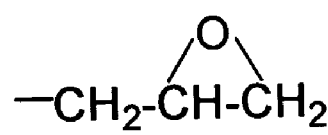  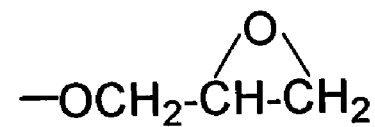
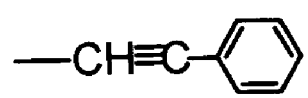  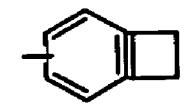

SULFONIC ACID GROUP-CONTAINING, PROTON-CONDUCTING POLYMER COMPOSITION, A SOLID ELECTROLYTE MEMBRANE AND A SOLID POLYMER FUEL CELL

CROSS-REFERENCE TO RELATED APPLICATIONS

This application is based upon and claims the benefit of priority from the prior Japanese Patent Application No. 2004-097398, filed on Mar. 30, 2004, the entire contents of which are incorporated herein by reference.

BACKGROUND OF THE INVENTION

1. Field of the Invention

The present invention relates to a solid electrolyte membrane for solid polymer fuel cells. More specifically, the present invention relates to a solid electrolyte membrane for proton-conducting, direct methanol fuel cells (referred to as DMFC, hereafter) or hydrogen fuel cells.

2. Description of the Related Art

A solid electrolyte membrane is an important material indispensable for electrochemical elements such as solid polymer fuel cells, temperature sensors, gas sensors and electrochromic devices. Among those uses, solid polymer fuel cells have high expectations as one of the features of new energy technologies in future. When a solid electrolyte membrane is used for a fuel cell, it is often called a proton-conducting membrane, since it plays a role of conducting protons.

Among the solid polymer fuel cells, an electric cell using methanol offers promising prospects as a power source for electric cars, since methanol can be supplied as a liquid fuel in the same way as gasoline. In addition, since it is easy to handle, it has high expectations as an electric cell for electric/electronic devices.

Methanol fuel cells are classified into two types: reforming type cells in which methanol is converted into a gas mixture mainly composed of hydrogen, using a reformer; and DMFC's that directly use methanol without using a reformer. Among them, practical application of DMFCs in electric/electronic portable devices is highly expected, because small and light-weight devices can be realized since no reformer is necessary.

On the other hand, organic polymer materials having sulfonic acid groups, carboxylic acid groups, phosphoric acid groups, or the like, are used for a solid electrolyte membrane that is an important element of a fuel cell. As the organic polymer materials, perfluorosulfonic acid containing polymers such as Nafion (trademark name) membrane of Du Pont and Dow membrane of Dow Chemical are conventionally used.

However, though perfluorosulfonic acid containing polymers described above have excellent proton conductivity, there is a problem of great tendency that methanol, which has a high affinity towards water, permeates from the anode side to the cathode side (methanol cross-over), when they are used for a solid electrolyte membrane of DMFCs. When the cross-over occurs, the supplied fuel (methanol) reacts directly with oxygen at the cathode, making it impossible to draw out the energy of methanol as electric power.

In the case of some proton-conducting membranes such as PBI used in Hydrogen fuel cells that do not involve water, the methanol cross-over has been reported to be small. However, in these polymers that have been doped with strong acids such as phosphoric acid or the like, for example, there is a problem that inorganic dopants leach out from the polymer with methanol/water solution, though the methanol cross-over is small.

Besides the above polymer, sulfonated polyphenylene ethers, polyether ketones, polyimides, polybenzoxazoles, polybenzothiazoles, etc. draw attention as materials with low methanol cross-over (see claims and paragraph 2-4 of Japanese Unexamined Patent Application Publication No. 2002-201269, for example). The major problems of these polymers are that sufficient proton conductivity can not be obtained, since appropriate ion channeling structures are hard to be formed in those materials, and also that they degrade under a strong-acid atmosphere, since they have a lot of CH bonds.

SUMMARY OF THE INVENTION

The present invention relates to a new solid electrolyte membrane. More specifically, the present invention is directed to providing an excellent solid electrolyte membrane with low methanol cross-over and high proton conductivity suitable for DMFCs. Other objects and advantages according to the present invention will be made clear from the following descriptions.

According to one aspect of the present invention, provided is an electrolyte composition comprising a sulfonic acid group-containing polymer having at least one structure unit selected from the group consisting of a structure unit represented by formula (1), a structure unit represented by formula (2), a structure unit represented by formula (3), and a structure unit represented by formula (4),

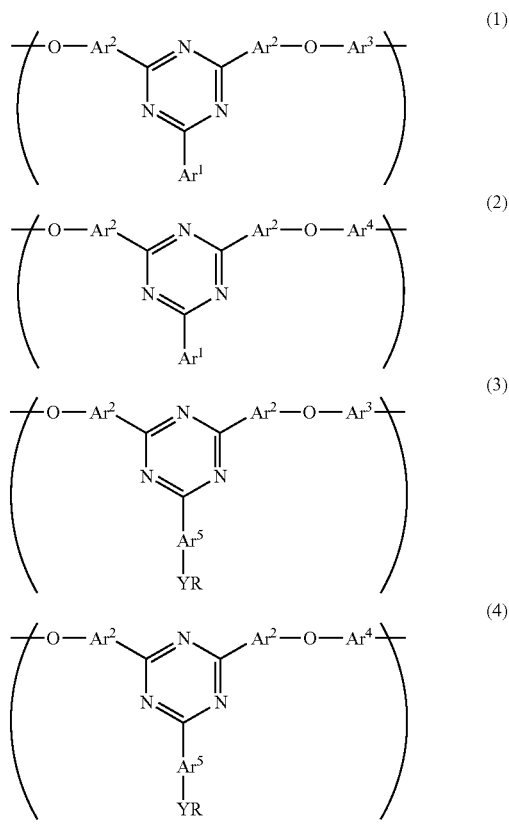

(in formulae (1)-(4), Y is, independently for each formula, O, S or a direct bond; R is, independently for each formula, a group having at least either one of an unsaturated bond and an epoxy bond; $Ar^1$ is, independently for each formula, a sulfonic acid group-containing monovalent aromatic ring that may comprise fluorine or a fluorine-containing substituent group; $Ar^2$ is, independently for each formula and from each other in each formula, a divalent aromatic ring that may comprise fluorine or a fluorine-containing substituent group; $Ar^3$ is, independently for each formula, a divalent group comprising an aromatic ring that may comprise fluorine or a fluorine-containing substituent group; $Ar^4$ is, independently for each formula, a divalent group comprising a sulfonic acid group-containing aromatic ring that may comprise fluorine or a fluorine-containing substituent group; and $Ar^5$ is a phenylene group that may have 1 to 4 fluorine atoms as substituents).

Preferable are that the sulfonic acid group-containing polymer is cross-linkable by an active energy ray irradiation treatment, heat treatment, or a combination thereof; that the sulfonic acid group-containing polymer is a homopolymer, a random copolymer, a block copolymer, or a mixture thereof; that $Ar^1$ is, independently for each formula, a sulfonic acid group-containing phenyl group that may comprise fluorine or a fluorine-containing substituent group; that the two $Ar^2$'s in each formula are phenylene groups that may comprise fluorine or a fluorine-containing substituent group; that $Ar^1$ comprises one or two sulfonic acid groups; that Y is a direct bond, and R is a group selected from the group consisting of $CH=CH_2$, $CH_2CH=CH_2$ and $CF=CF_2$; that at least either one of $Ar^3$ and $Ar^4$ has a structure unit selected from the group consisting of a phenylene sulfone structure unit, a phenylene sulfoxide structure unit, a phenylene ketone structure unit, a phenylene ether structure unit, a benzoxazole structure unit, a benzothiazole structure unit and a triphenyl phosphine oxide structure unit; that the structure unit represented by formula (1) is obtained by reacting a compound represented by formula (5) and a compound represented by formula (6),

(5)

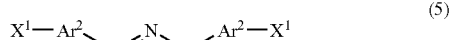
(6)

F—$Ar^3$—F (7)

——OH (9)

(10)

(in formulae (5) and (6), $X^1$ is, independently from each other, a group represented by formula (9) or (10); in formula (10), $R^1$ is, independently from each other, an alkyl group that may be branched; the other symbols have the same meanings as in formulae (1) to (4); and the sulfonic acid group in $Ar^1$ may be a salt of an alkali metal or an alkaline earth metal); that the structure unit represented by formula (2) is obtained by reacting a compound represented by formula (5) and a compound represented by formula (7),

(5)

F—$Ar^4$—F (7)

——OH (9)

(10)

(in formulae (5) and (7), $X^1$ is, independently from each other, a group represented by formula (9) or (10); in formula (10), $R^1$ is, independently from each other, an alkyl group that may be branched; the other symbols have the same meanings as in formulae (1) to (4); and the sulfonic acid group in $Ar^1$ and $Ar^4$ may be a salt of an alkali metal or an alkaline earth metal); that the structure unit represented by formula (3) is obtained by reacting a compound represented by formula (8) and a compound represented by formula (6),

(8)

F—$Ar^3$—F (6)

——OH (9)

(10)

(in formulae (8) and (6), $X^2$ is, independently from each other, a group represented by formula (9) or (10); in formula (10), $R^1$ is, independently from each other, an alkyl group that may be branched; and the other symbols have the same meanings as in formulae (1) to (4)); that the structure unit represented by formula (4) is obtained by reacting a compound represented by formula (8) and a compound represented by formula (7),

(8)

-continued $$F-Ar^4-F \quad (7)$$

$$-OH \quad (9)$$

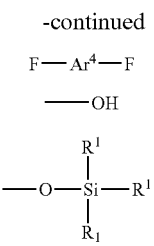
(10)

(in formulae (8) and (7), $X^2$ is, independently from each other, a group represented by formula (9) or (10); in formula (10), $R^1$ is, independently from each other, an alkyl group that may be branched; the other symbols have the same meanings as in formulae (1) to (4); and the sulfonic acid group in $Ar^4$ may be a salt of an alkali metal or an alkaline earth metal); that the sulfonic acid group-containing polymer has a number-average molecular weight (Mn) of 5,000-10,000,000; and that the electrolyte composition is obtained by subjecting the above-described electrolyte composition to an active energy ray irradiation treatment, a heat treatment, or a combination thereof.

By this aspect of the present invention, a new solid electrolyte membrane is provided. This solid electrolyte membrane can be used in DMFCs, reforming type methanol fuel cells, hydrogen fuel cells, etc., as the solid electrolyte membrane that is stable in a strong acid atmosphere. When used for DMFCs, it can serve as a solid electrolyte membrane with low methanol cross-over and high proton conductivity, while swelling in an aqueous methanol solution is restrained.

According to other aspects of the present invention, provided are a solid electrolyte membrane comprising the above-described electrolyte composition; and a solid electrolyte membrane obtained by subjecting the above-described electrolyte composition to an active energy ray irradiation treatment, a heat treatment, or a combination thereof.

By these aspects of the present invention, low methanol cross-over and high proton conductivity are realized.

According to another aspect of the present invention, provided is a method for manufacturing a solid electrolyte membrane, wherein the above-described electrolyte composition comprises an organic solvent, the electrolyte composition comprising the organic solvent is applied to a substrate, and the solvent is removed thereafter.

Preferable are that after the removal of the solvent, an active energy ray irradiation treatment, a heat treatment, or a combination thereof, is performed; and that a hot rolling (that is, hot press) treatment is performed after the removal of the solvent, or after the active energy ray irradiation treatment, heat treatment or combination thereof.

By this aspect of the present invention, a solid electrolyte membrane having low methanol cross-over and high proton conductivity is realized.

According to other aspects of the present invention, provided are a solid polymer fuel cell using the above-described solid electrolyte membrane, and a solid polymer fuel cell using a solid electrolyte membrane manufactured by the above-described method. A highly efficient solid polymer fuel cell can be obtained.

All in all, by the present invention, a new solid electrolyte membrane is provided. This solid electrolyte membrane can be used for DMFCs, reforming type methanol fuel cells, hydrogen fuel cells, etc., as a solid electrolyte membrane that is stable in a strong acid atmosphere. When used for DMFCs, it can serve as a solid electrolyte membrane having a low methanol cross-over property and a high proton conductivity, while swelling in an aqueous methanol solution is restrained. Furthermore, the present invention provides an electrolyte composition for obtaining such a solid electrolyte membrane.

BRIEF DESCRIPTION OF THE DRAWINGS

FIG. 1 shows examples of $Ar^1$ and $Ar^2$;
FIG. 2 shows examples of $Ar^3$;
FIG. 3 shows examples of $Ar^4$;
FIG. 4 shows examples of structures of polymers according to the present invention;
FIG. 13 shows examples of R.

DESCRIPTION OF THE PREFERRED EMBODIMENTS

Figure 5:
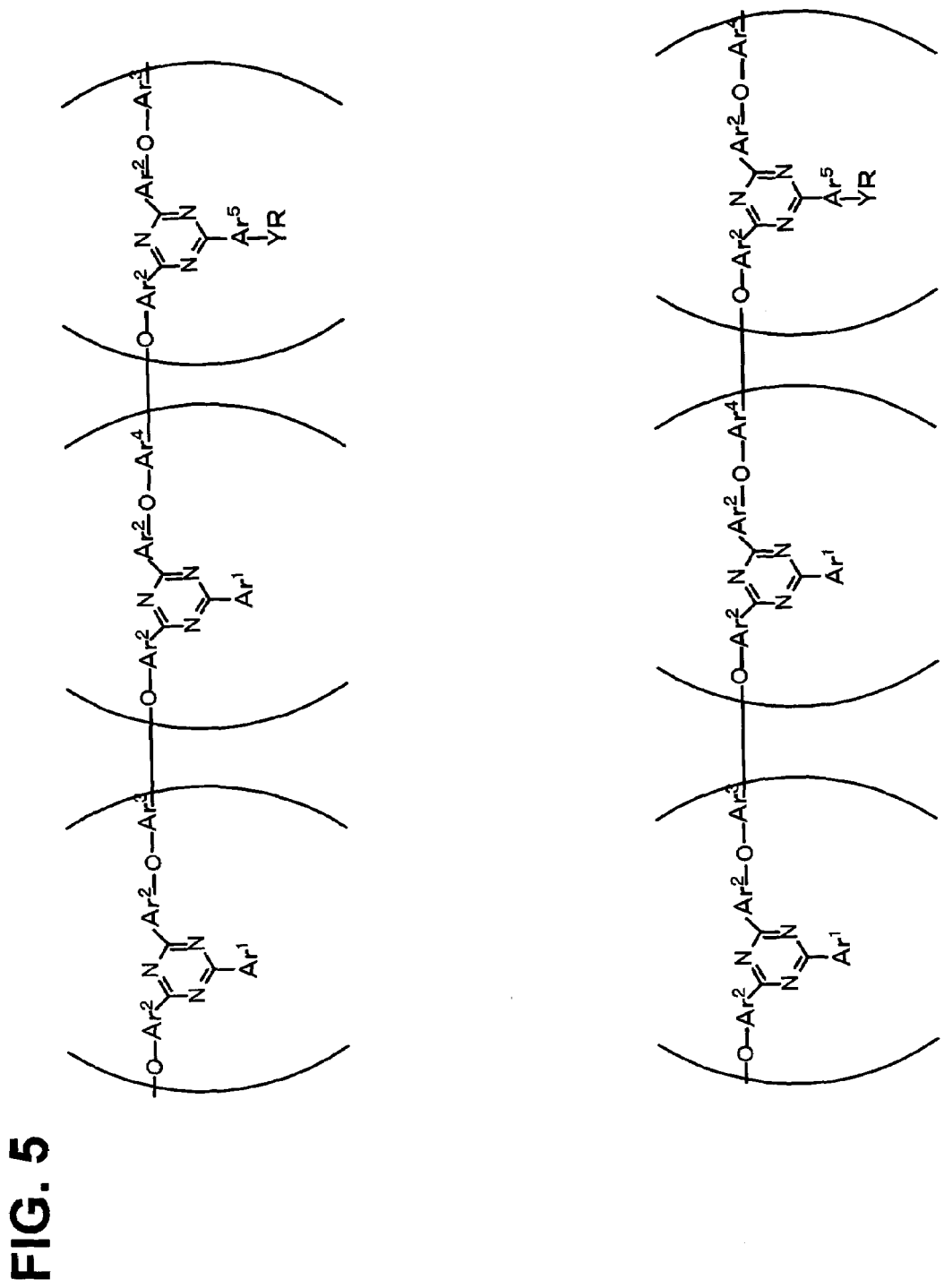
FIG. 5 shows examples of structures of polymers according to the present invention.

Embodiments according to the present invention will now be described below, using drawings, formulae, examples, etc. These drawings, formulae, examples, etc., and descriptions are for demonstrating the present invention, and do not limit the scope of the invention. Needless to say, other embodiments can be included in the scope of the present invention as long as they conform to the essential character according to the present invention.

The electrolyte composition according to the present invention comprises a sulfonic acid group-containing polymer. This sulfonic acid group-containing polymer has at least one structure unit selected from the group consisting of a structure unit represented by formula (1), a structure unit represented by formula (2), a structure unit represented by formula (3), and a structure unit represented by formula (4).

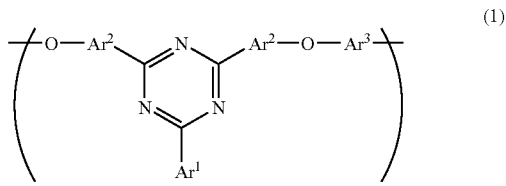
(1)

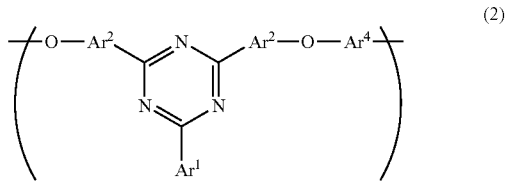
(2)

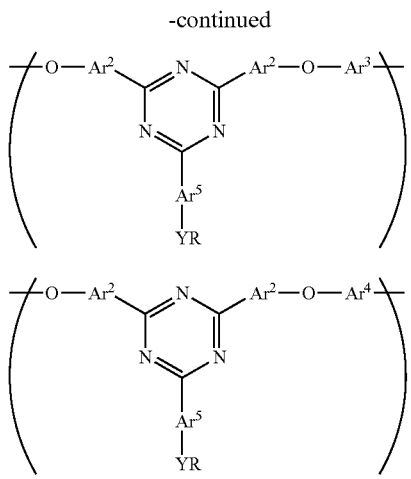

A polymer electrolyte membrane prepared by using an electrolyte composition comprising the polymer, makes formation of an ion channeling structure easier by means of the polymeric structure having a sulfonic acid-group, with the result that a necessary level of proton conductivity is realized.

In formulae (1)-(4), Y is, independently for each formula, O, S or a direct bond, and R is, independently for each formula, a group having at least either one of an unsaturated bond and an epoxy bond. $Ar^1$ is, independently for each formula, a sulfonic acid group-containing monovalent aromatic ring that may comprise fluorine or a fluorine-containing substituent group. $Ar^2$ is, independently for each formula and from each other in each formula, a divalent aromatic ring that may comprise fluorine or a fluorine-containing substituent group. $Ar^3$ is, independently for each formula, a divalent group comprising an aromatic ring that may comprise fluorine or a fluorine-containing substituent group. $Ar^4$ is, independently for each formula, a divalent group comprising a sulfonic acid group-containing aromatic ring that may comprise fluorine or a fluorine-containing substituent group. $Ar^5$ is a phenylene group that may have 1 to 4 fluorine atoms as substituents. It is to be noted that as an aromatic ring according to the present invention enumerated are, unless otherwise indicated, a condensed ring and a heterocycle such as a naphthalene ring, anthracene ring, pyrimidine ring, pyrazine ring, and thiophene ring, besides one containing one or more benzene rings.

Examples of $Ar^1$ to $Ar^4$ are shown in FIGS. 1 to 3. In FIG. 1, one sulfonic acid group is located on the benzene ring. However, any number of sulfonic acid groups may be located on a benzene ring, if possible.

According to the present invention, a polymer structure having a sulfonic acid group can be easily synthesized by introducing a triazine skeleton. An ion channel structure for acquiring a high proton conductivity is realized by the polymer structure having a sulfonic acid group.

$Ar^1$ may preferably be, independently from each other, a phenyl group containing a sulfonic acid group that may have fluorine or a substituent group comprising fluorine. Both $Ar^2$ in each formula are preferably a phenylene group that may have fluorine or a substituent group comprising fluorine. $Ar^1$ with any number of sulfonic acid groups may be accepted, if possible, but one with one or two sulfonic acid groups is preferable. It is easy to be synthesized and is stable in a strong acid atmosphere, with the result that a solid electrolyte membrane having a low methanol cross-over property and a high proton conductivity is realized.

Furthermore, low methanol cross-over can be obtained by incorporating, to the main polymer chain, a phenylene sulfone structure unit, a phenylene sulfoxide structure unit, a phenylene ketone structure unit, a phenylene ether structure unit, a benzoxazole structure unit, a benzothiazole structure unit, a triphenyl phosphine oxide structure unit, or the like, as shown in $Ar^3$ in FIG. 2 and $Ar^4$ in FIG. 3.

Also, as shown in $Ar^1$ and $Ar^2$ in FIG. 1, $Ar^3$ in FIG. 2 and $Ar^4$ in FIG. 3, the number of CH bonds can be reduced by introducing fluorine onto the aromatic ring or another group. It is preferable that fluorine replaces hydrogen in a ring. However, fluorine that is bound with a ring through a carbon atom or the like may also be accepted.

Furthermore, by introducing an unsaturated bond or an epoxy bond by means of R, a network structure by polymerization and cross-linking can be implemented, and accordingly, can make a polymer electrolyte membrane that does not degrade in water/methanol or in a strong acid atmosphere. It is preferable that this unsaturated bond or epoxy bond is used for polymerization and cross-linking with active energy rays such as ultraviolet (UV) rays, heat, or a combination thereof.

The sulfonic acid group-containing polymer having at least one structure unit selected from the group consisting of a structure unit represented by formula (1), a structure unit represented by formula (2), a structure unit represented by formula (3), and a structure unit represented by formula (4) may be a homopolymer composed of only each of the structure units, a block copolymer composed of an arbitrary combination of these structure units, or a random copolymer composed of an arbitrary combination of these structure units. Furthermore, it may be a copolymer of any of the structure units and a different structure unit. A mixture of any of these polymers may be accepted. It is possible to adjust the physical properties, chemical properties, degree of cross-linking, content of each group of the polymer or polymers, by introducing other structure units, or by blending with other materials. For example, the content of the sulfonic acid group can be adjusted.

Examples of these polymer structures are shown in FIGS. 4 and 5. The parentheses in FIGS. 4 and 5 indicate respective structure units. There is no particular limitation to the number of repeating units, and it may be arbitrarily determined according to the real requirements.

Furthermore, it is preferable that the sulfonic acid group-containing polymer according to the present invention has a number-average molecular weight (Mn) of 5,000 to 10,000,000, from the viewpoint of film forming properties. When the sulfonic acid group-containing polymer according to the present invention is a mixture, the Mn is determined by handling the mixture as a single polymer.

The degree of polymerization of a polymer in the electrolyte composition according to the present invention can be easily raised by the reaction of a group comprising an unsaturated bond or epoxy bond. Also when cross-linking is possible, a network structure can be introduced into the electrolyte composition to easily form a polymer electrolyte membrane that is hard to swell in water/methanol or in a strong acid atmosphere.

When a different compound is present in the electrolyte composition according to the present invention, the compound may have a group comprising an unsaturated bond or epoxy bond, for the purpose of cross-linking. The same effect can be expected. This compound may be an oligomer or polymer. Divinylbenzene, diglycidyl ether bisphenol-A, bis (trifluorovinyloxybenzene), etc. may be examples.

Any group may be used as the group represented by R that has at least one unsaturated bond or epoxy bond, and a triple bond may be used besides a double bond. A plurality of unsaturated bonds may be present in R. FIG. 13 shows examples. It is preferable that R comprises a group selected from the group consisting of $CH=CH_2$, $CH_2CH=CH_2$ and $CF=CF_2$.

Such a group having an unsaturated bond and/or an epoxy bond can be easily introduced, for example, by Grignard reaction between a compound having an unsaturated bond and a triazine ring.

The electrolyte composition according to the present invention that has a group comprising an unsaturated bond is, in most cases, cross-linkable with an active energy ray irradiation treatment, a heat treatment, or a combination of these treatments, as described above. Accordingly, formation of a film using the composition, followed by cross-linking is preferable, since it provides a polymer electrolyte membrane that is hard to swell, and also chemically stable in water/methanol or in a strong acid atmosphere. It is to be noted that UV rays are preferable as the active energy rays according to the present invention. An electrolyte composition according to the present invention also includes those that have been subjected to an active energy ray irradiation treatment, a heat treatment, or a combination thereof, as described above.

An example of the manufacturing process of an electrolyte composition according to the present invention is as follows.

The structure unit represented by formula (1) can be obtained by reacting a compound represented by formula (5) and a compound represented by formula (6), for example. Furthermore, the structure unit represented by formula (2) can be obtained by reacting a compound represented by formula (5) and a compound represented by formula (7), for example. The structure unit represented by formula (3) can be obtained by reacting a compound represented by formula (8) and a compound represented by formula (6), for example. The structure unit represented by formula (4) can be obtained by reacting a compound represented by formula (8) and a compound represented by formula (7), for example.

Figure 6:
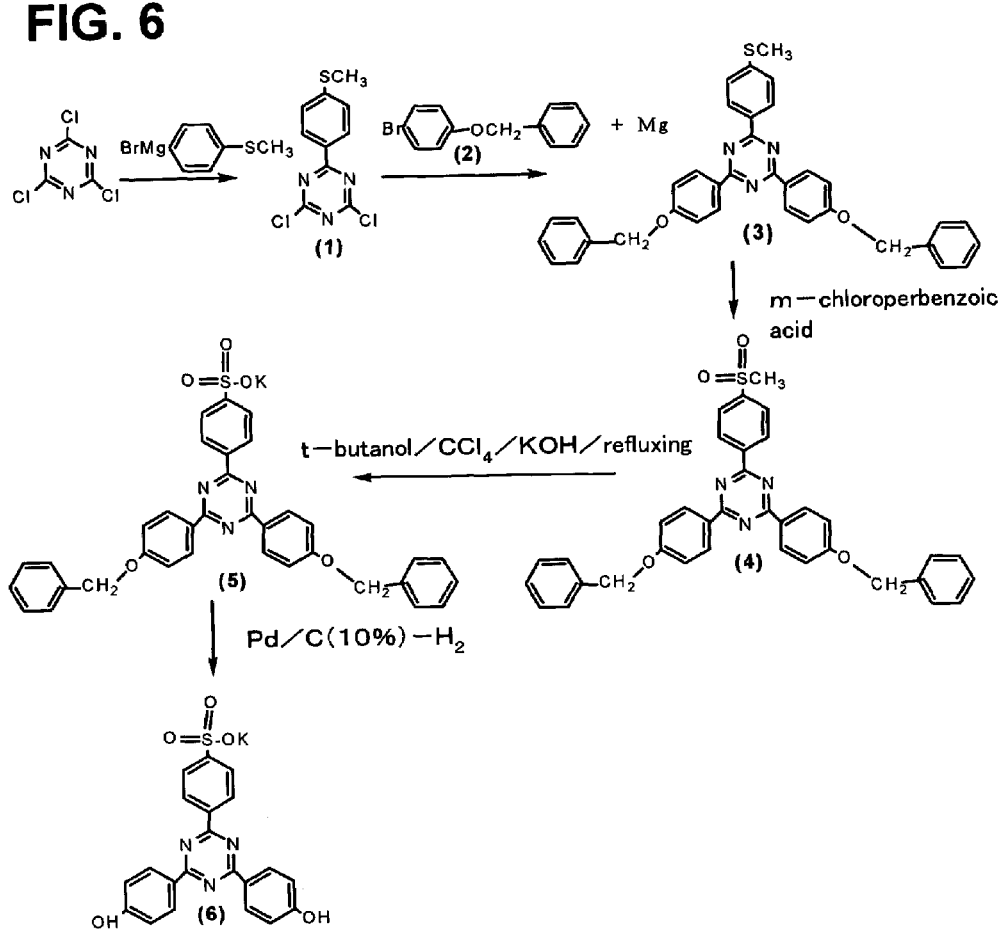
FIG. 6 shows an exemplary synthesis route of a monomer according to the present invention.
Figure 7:
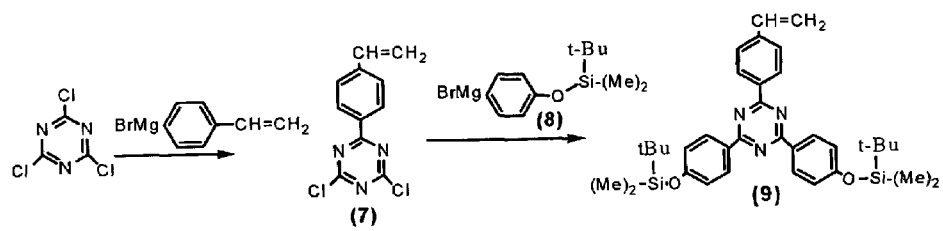
FIG. 7 shows an exemplary synthesis route of a monomer according to the present invention.

Among the above, the compound represented by formula (5) can be synthesized, for example, via a route shown in FIG. 6, and the compound represented by formula (8) can be synthesized, for example, via a route shown in FIG. 7. In the figures, the compound represented by numeral (6) corresponds to the compound represented by formula (5), and the compound represented by numeral (9) corresponds to the compound represented by formula (8).

It is to be noted that in the symbols in FIGS. (5) to (8), $X^1$ and $X^2$ are, independently from each other and independently in each formula, a group represented by formula (9) or (10). In formula (10), $R^1$ is, independently from each other, an alkyl group that may be branched. The other symbols have the same meanings as in formulae (1) to (4), though the sulfonic acid group in $Ar^1$ and $Ar^4$ may be a salt of an alkali metal or an alkaline earth metal. That is, $SO_3M$ (where M is an alkali metal or the like) may be used instead of $SO_3H$. It is possible to make $SO_3M$ into $SO_3H$ easily by treating with a strong acid.

Any known manufacturing process other than the above-described processes may be employed to obtain the electrolyte composition according to the present invention. Any of dimerization, oligomerization or polymerization may be employed. Accordingly, if the sulfonic acid group-containing polymer having a structure unit represented by any of formulae (1)-(4) is a homopolymer, it can be obtained by polymerization. When it is a block copolymer, it can be obtained, for example, by subjecting an oligomer obtained by oligomerization or a polymer, to a redistribution reaction or polymerization, together with a different oligomer or polymer.

FIGS. 8 to 12 show examples of sulfonic acid group-containing polymer structures according to the present invention thus obtained. In FIGS. 8 to 12, m, n, p and q can be arbitrarily determined independently from each other. In the figures, polymers 1 and 4 are homopolymers composed of only the structure represented by formula (1), polymers 2 and 5 are copolymers composed of the structure represented by formula (1) and the structure represented by formula (2), and polymer 3 is a copolymer composed of the structure represented by formula (1), the structure represented by formula (2), the structure represented by formula (3), and the structure represented by formula (4). It is to be noted that polymers 1 to 5 have $SO_3K$ instead of $SO_3H$, wherein the $SO_3K$ can be easily changed into $SO_3H$ by a treatment with an acid, as described above.

By the present invention, a new electrolyte composition is provided. From this electrolyte composition, it is possible to provide a solid electrolyte membrane that is chemically stable in a strong acid atmosphere, and can be used for DMFCs, reforming type methanol fuel cells, hydrogen fuel cells, etc. When used for DMFCs, it can serve as a solid electrolyte membrane having low methanol cross-over and high proton conductivity.

It is to be noted that other polymers as well as solvents, catalysts and additives may also be present in the electrolyte composition according to the present invention, besides the above-described sulfonic acid group-containing polymer. Polyacrylate and polysiloxane are examples of the other polymers, dimethyl acetamide, dimethyl formamide, N-methyl pyrrolidone, dimethyl sulfoxide and m-cresol are examples of the solvents, and imidazole, triphenyl phosphine, 2,2'-azobisisobutyronitrile are examples of the catalysts.

A solid electrolyte membrane can be formed from the electrolyte composition according to the present invention obtained in this way. In this case, when the electrolyte composition contains a component that is cross-linkable, an

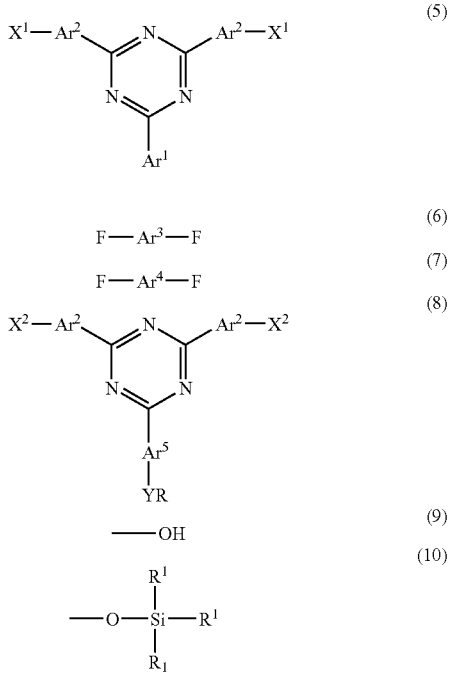

excellent membrane can be manufactured by an active energy ray irradiation treatment, a heat treatment, or a combination thereof.

When the electrolyte composition according to the present invention contains an organic solvent, a solid electrolyte membrane can be easily manufactured by applying this electrolyte composition onto a substrate, followed by removal of the solvent. After the removal of a solvent, an active energy ray irradiation treatment, a heat treatment, or a combination thereof can be performed. Any material can be used for the substrate as long as it is inactive to the electrolyte composition and the solvent, and it can form a membrane of the electrolyte composition.

Furthermore, it is also useful in many cases to perform a hot rolling (that is, hot press) treatment, after the removal of a solvent, or after an active energy ray irradiation treatment, a heat treatment, or a combination thereof. Adhesion between the catalyst layers and the electrolyte membrane can be improved. A temperature of from 100 to 160° C. and a pressure of from 10 to 150 kg/cm$^2$ are favorable conditions for the hot rolling treatment.

The solid electrolyte membrane thus obtained can be used for a solid polymer fuel cell, especially for a DMFC, a reforming type methanol fuel cell, a hydrogen fuel cell, etc. It can serve as a solid electrolyte membrane that is chemically stable in a strong acid atmosphere. When used for a DMFC, it can serve as a solid electrolyte membrane having low methanol cross-over and high proton conductivity.

EXAMPLES

Next, examples of the present invention will be explained in detail, referring to FIGS. 6 to 12. The numbers for the compounds and polymers in the examples correspond to those in FIGS. 6 to 12.

(Synthesis of Monomers)

Example 1

Manufacuring of 2,4-dichloro-6-(4-thiomethylphenyl)-1,3,5-triazine (compound 1): FIG. 6

A solution obtained by dissolving 4-bromothioanisole (18.27 g, 0.09 mol) and magnesium (2.64 g, 0.11 mol) into tetrahydrofuran (THF) (200 mL), was stirred at 30° C. for two hours, and then, refluxed for another two hours. This solution was added to a solution of cyanuric chloride (21.58 g, 0.120 mol) in THF (200 mL) at −20° C., and the mixture was stirred at −20° C. for five hours.

The solvent was removed under a reduced pressure, the solid product thus formed was dissolved into dichloromethane, and washed with water twice. The organic layer was dried over anhydride MgSO$_4$, and the solvent was distilled off.

The crude product was recrystallized in dichloromethane/n-hexane. The yield was 80%. $^1$H-NMR results (CDCl$_3$, δ ppm): 8.41 (d, 2H, ArH-triazine), 7.33 (d, 2H, ArH-triazine), and 2.56 (s, 3H, SCH$_3$).

Example 2

Manufacuring of 4-benzyloxybromobenzene (compound 2): FIG. 6

To a solution composed of p-bromophenol (17.3 g, 0.1 mol) and dry DMF (100 mL), anhydride K$_2$CO$_3$ (8.28 g, 0.06 mmol) and benzyl bromide (25.6 g, 0.15 mmol) were added. The mixture was stirred at 80° C. under a nitrogen atmosphere for six hours. Then, the reaction mixture was charged into 500 mL of ice water.

The solid product was subjected to filtering with suction, drying and recrystallization in methanol. The yield was 85%. $^1$H-NMR results (CDCl$_3$, δ ppm): 7.42-7.30 (m, 7H, ArH), 6.85 (d, 2H, ArH), and 5.02 (s, 2H, OCH$_2$Ar).

Example 3

Manufacturing of 2,4-bis(4-benzyloxyphenyl)-6-(4-thiomethylphenyl)-1,3,5-triazine (compound 3): FIG. 6

A THF solution (150 mL) of compound 1 (27.2 g, 0.1 mol) was added to a solution obtained by dissolving 4-benzyloxyphenylmagnesium bromide prepared from compound 2 (78.9 g, 0.30 mol) and magnesium (7.92 g, 0.33 mol), into THF (300 mL). The mixture was refluxed for ten hours, and then, the solvent was removed under a reduced pressure. The remaining solid was dissolved into dichloromethane, and washed with water twice. The organic layer was dried over anhydride MgSO$_4$, and the solvent was distilled off.

The crude product was purified by column chromatography on silica gel, using hexane/methylene chloride (volume ratio=1:1) as a solvent. The yield was 60%. $^1$H-NMR results (CDCl$_3$, δ ppm): 8.68 (d, 4H, ArH-triazine), 8.28 (d, 2H, ArH-triazine), 7.49-7.36 (m, 12H, ArH), 7.06 (d, 4H, ArH-triazine), 5.17 (s, 4H, OCH$_2$Ar), and 2.55 (s, 3H, CH$_3$).

Example 4

Manufacturing of 2,4-bis(4-benzyloxyphenyl)-6-(4-sulfonemethylphenyl)-1,3,5-triazine (compound 4): FIG. 6

A solution composed of compound 3 (41.7 g, 0.1 mol), m-chloroperbenzoic acid (55.7 g, 0.35 mmol) and dry methylene chloride (400 mL) was stirred at room temperature for three hours. The reaction mixture was washed with 20 wt. % Na$_2$SO$_3$ solution (twice, each 200 mL), 20 wt. % NaHCO$_3$ solution (twice, each 200 mL), and deionized water, and dried over anhydride MgSO$_4$. The solvent was distilled off under a reduced pressure, and a pale yellow solid was filtered out.

The product was recrystallized in ethanol. The yield was 66%. $^1$H-NMR results (CDCl$_3$, δ ppm): 8.84 (d, 2H, ArH-triazine), 8.62 (d, 4H, ArH-triazine), 8.14 (d, 2H, ArH-triazine), 7.50-7.35 (m, 10H, ArH), 7.22 (d, 4H, ArH-triazine), 5.23 (s, 4H, OCH$_2$Ar), and 3.31 (s, 3H, SO$_2$CH$_3$).

Example 5

Manufacturing of potassium 2,4-bis(4-benzyloxyphenyl)-6-(4-sulfonatephenyl)-1,3,5-triazine (compound 5): FIG. 6

A solution composed of compound 4 (10 g), a KOH powder (50 g), t-butanol (10 mL), H$_2$O (5 mL) and CCl$_4$ (100 mL) was stirred at 80° C. for two hours. The solvent was distilled off. The crude product was dissolved into H$_2$O, and excess NaCl was added to precipitate the product. Then, it was recrystallized in methanol/H$_2$O (volume ratio=8/2).

The purified solid was dried under a reduced pressure at 80° C. for 12 hours. The yield was 70%. $^1$H-NMR results (CDCl$_3$, δ ppm): 8.67 (d, 2H, ArH-triazine), 8.58 (d, 4H, ArH-triazine), 7.92 (d, 2H, ArH-triazine), 7.50-7.35 (m, 10H, ArH), 7.19 (d, 4H, ArH-triazine), and 5.21 (s, 4H, OCH$_2$Ar).

Example 6

Manufacturing of potassium 2,4-bis(4-hydroxyphenyl)-6-(4-sulfonatephenyl)-1,3,5-triazine (compound 6): FIG. 6

A solution composed of compound 5 (10 g), 10 wt. % Pd—C (1.0 g), and THF/H$_2$O (volume ratio=10:2, 50 mL), was stirred in a H$_2$ atmosphere for 24 hours. The reaction mixture was filtered with celite, and the solvent was distilled off under a reduced pressure.

The crude product was recrystallized in ethanol/H$_2$O (volume ratio=10/1). The yield was 78%. $^1$H-NMR results (CDCl$_3$, δ ppm): 8.66 (d, 2H, ArH-triazine), 8.59 (d, 4H, ArH-triazine), 7.83 (d, 2H, ArH-triazine), and 6.98 (d, 4H, ArH-triazine).

Example 7

Manufacturing of 2,4-dichloro-6-(4-vinylphenyl)-1,3,5-triazine (compound 7): FIG. 7

A solution formed by dissolving 4-bromostyrene (18.3 g, 0.1 mol) and magnesium (2.64 g, 0.11 mol) into THF (200 mL) was stirred at 30° C. for two hours, and then, refluxed for two hours. This solution was added to a solution of cyanuric chloride (21.58 g, 0.120 mol) into THF (200 mL) at −20° C., and the mixture was stirred at −20° C. for five hours. The solvent was distilled off under a reduced pressure, the remaining solid was dissolved into dichloromethane and washed with water twice. The organic layer was dried over anhydride MgSO$_4$, and the solvent was distilled off.

The crude product was recrystallized in dichloromethane/n-hexane. The yield was 85%. $^1$H-NMR results (CDCl$_3$, δ ppm): 8.42 (d, 2H, ArH-triazine), 7.51 (d, 2H, ArH-triazine), 6.76 (dd, 1H, CH=C), 5.90 (d, 1H, C=CH$_2$), and 5.43 (d, 1H, C=CH$_2$).

Example 8

Manufacturing of 2,4-bis(4-(t-butyldimethylsilyloxyphenyl)-6-(4-vinylphenyl)-1,3,5-triazine (compounds 9): FIG. 7

A solution formed by dissolving compound 7 (25.2 g, 0.1 mol) into THF (150 mL), was added to a solution formed by dissolving 4-(t-butyldimethylsilyloxy) phenylmagnesium bromide that had been prepared from 4-(t-butyldimethylsilyloxy)phenyl bromide (86.4 g, 0.30 mol) and magnesium (7.92 g, 0.33 mol), into THF (300 mL), and then, the reaction mixture was stirred at 80° C. for ten hours. The solvent was removed under a reduced pressure, and the remaining solid was dissolved in dichloromethane, and washed with water twice. The organic layer was dried over anhydride MgSO$_4$, and the solvent was distilled off.

The crude product was purified by column chromatography on alumina, using hexane:ethyl acetate (volume ratio=10:1) as a solvent. The yield was 70%. $^1$H-NMR results (CDCl$_3$, δ ppm): 8.44-8.35 (m, 6H, ArH-triazine), 7.51 (d, 2H, ArH-triazine), 6.85 (d, 4H, ArH-triazine), 6.72 (dd, 1H, CH=C), 5.85 (d, 1H, C=CH$_2$), 5.27 (d, 1H, C=CH$_2$), 0.99 (s, 18H, t-BuCH$_3$), and 0.25 (s, 12H, OSiCH$_3$).

Example 9

Figure 11:
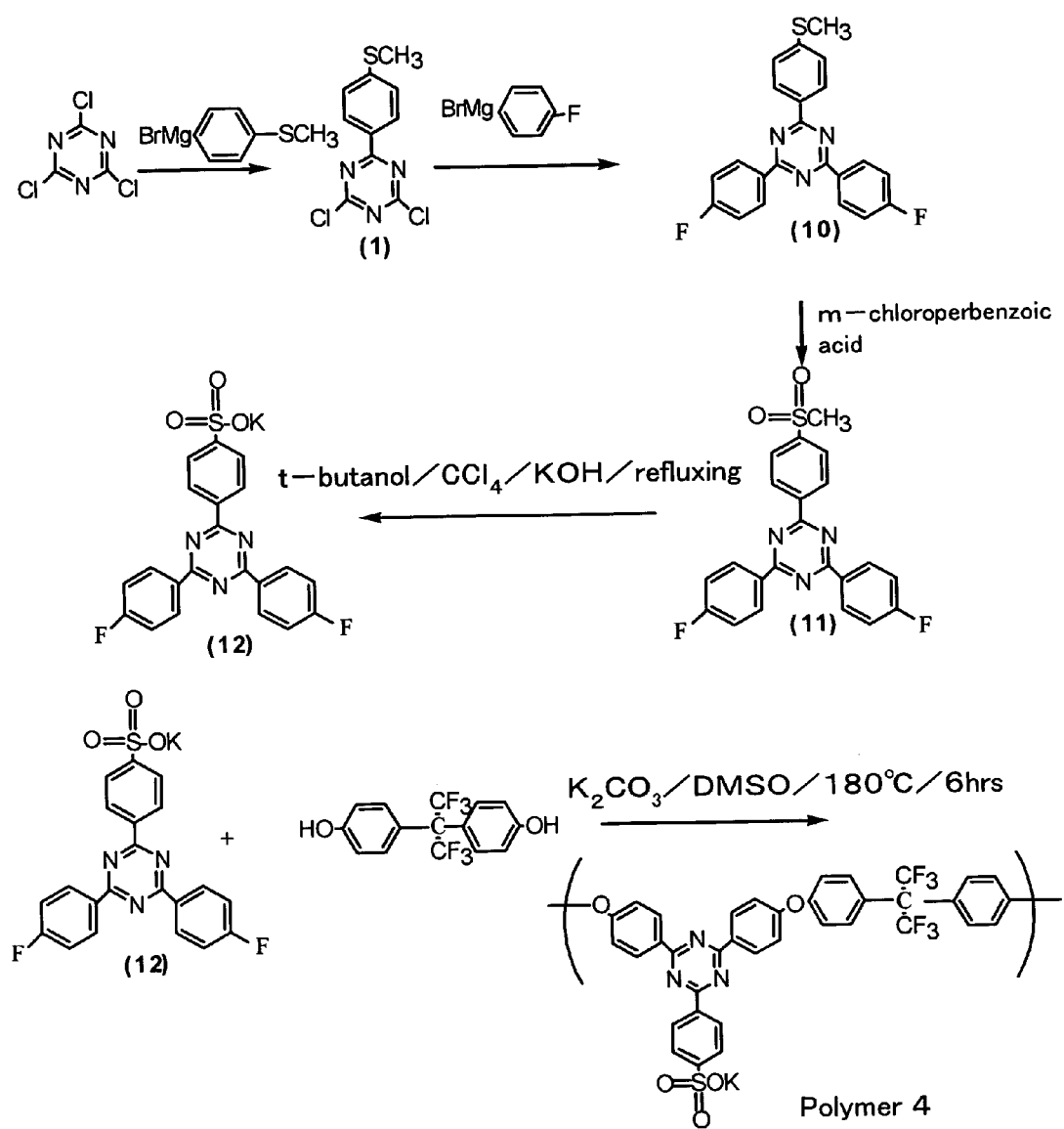
FIG. 11 shows exemplary synthesis routes of a monomer and a polymer according to the present invention.

Manufacturing of 2,4-bis(4-fluorophenyl)-6-(4-thiomethylphenyl)-1,3,5-triazine (compound 10): FIG. 11

A solution formed by dissolving compound 1 (27.2 g, 0.1 mol) into THF (150 mL), was added to a solution formed by dissolving 4-bromophenylmagnesium bromide that had been prepared from 4-bromofluorobenzene (52.5 g, 0.30 mol) and magnesium (7.92 g, 0.33 mol), into THF (300 mL). The mixture was refluxed for ten hours, and then, the solvent was removed under a reduced pressure. The remaining solid was dissolved into dichloromethane, and washed with water twice. The organic layer was dried over anhydride MgSO$_4$, and the solvent was distilled off.

The crude product was purified by column chromatography on silica gel, using hexane:methylene chloride (volume ratio=1:0.5) as a solvent. The yield was 70%. $^1$H-NMR results (CDCl$_3$, δ ppm): 8.72 (m, 4H, ArH-triazine), 8.30 (d, 2H, ArH-triazine), 7.40 (d, 2H, ArH-triazine), 7.07 (m, 4H, ArH-triazine), and 2.55 (s, 3H, SCH$_3$).

Example 10

Manufacturing of 2,4-bis(4-fluorophenyl)-6-(4-sulfonemethylphenyl)-1,3,5-triazine (compound 11): FIG. 11

A solution formed from compound 10 (39.1 g, 0.1 mol), m-chloroperbenzoic acid (55.7 g, 0.35 mmol) and dry methylene chloride (400 mL), was stirred at room temperature for three hours. The reaction mixture was washed with 20% Na$_2$SO$_3$ (each 200 mL, twice), 20% NaHCO$_3$ (each 200 mL, twice), and deionized water, and then, dried over anhydride MgS$_4$. The solvent was distilled off under a reduced pressure, and a pale yellow solid was filtered out. The product was recrystallized in ethanol. The yield was 70%. $^1$H-NMR results (CDCl$_3$, δ ppm): 8.86 (d, 2H, ArH-triazine), 8.70 (m, 4H, ArH-triazine), 8.20 (d, 2H, ArH-triazine), 7.12 (m, 4H, ArH-triazine), and 3.31 (s, 3H, SO$_2$CH$_3$).

Example 11

Manufacturing of potassium 2,4-bis(4-fluorophenyl)-6-(4-sulfonatephenyl)-1,3,5-triazine (compound 12): FIG. 11

A solution composed of compound 11 (10 g), a KOH powder (50 g), t-butanol (10 mL), H$_2$O (5 mL) and CCl$_4$ (100 mL) was stirred at 80° C. for two hours. The solvent was distilled off, and the crude product was dissolved into H$_2$O, excess NaCl was added and the product was precipitated. The product was recrystallized in methanol/H$_2$O (volume ratio=8/2). The purified solid was dried under a reduced pressure at 80° C. for 12 hours. The yield was 60%. $^1$H-NMR results (CDCl$_3$, δ ppm): 8.70 (d, 2H, ArH-triazine), 8.61 (m, 4H, ArH-triazine), 8.00 (d, 2H, ArH-triazine), and 7.15 (m, 4H, ArH-triazine).

Example 12

Figure 8:
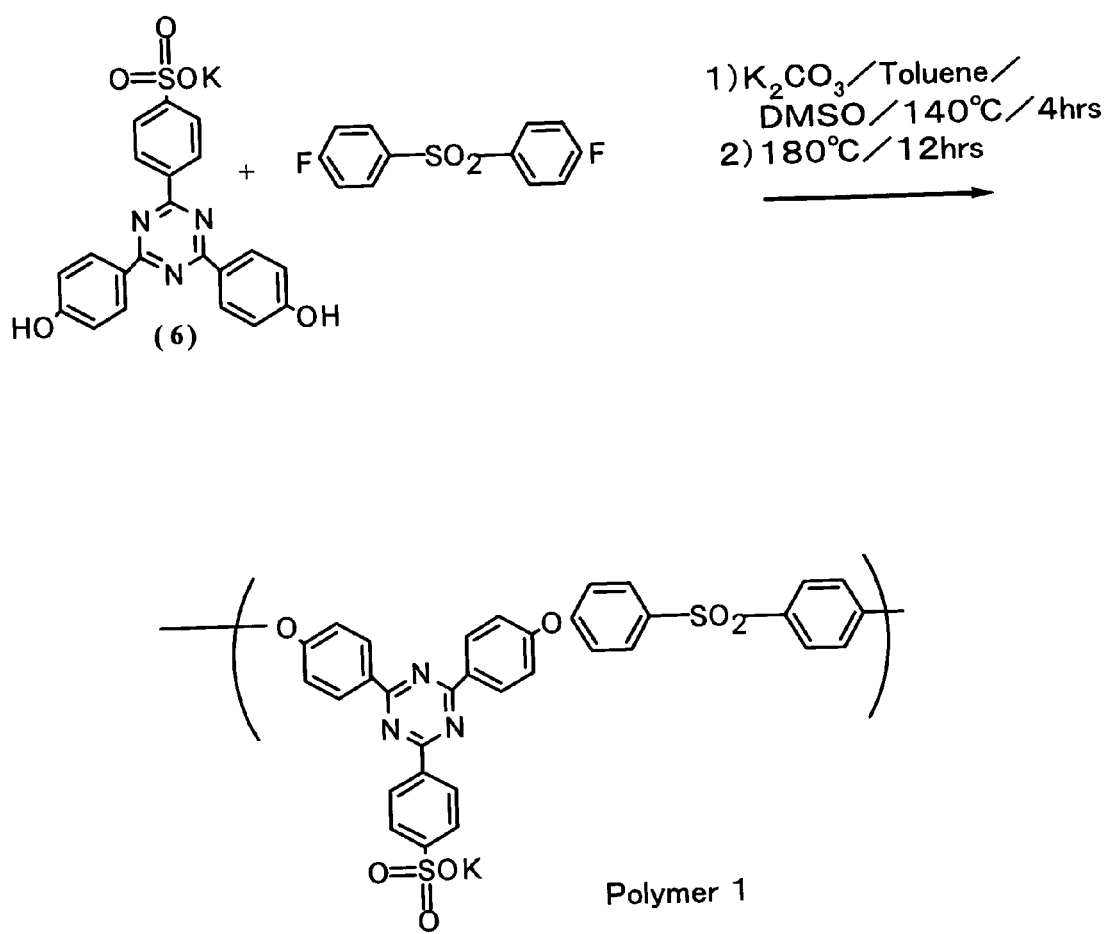
FIG. 8 shows an exemplary synthesis route of a polymer according to the present invention.

Manufacturing of Polymer 1: FIG. 8

To a 100 mL three-necked, round-bottom flask, fitted with a condenser, a Dean-Stark arm, and a nitrogen purge system were added compound 6 (4.59 g, 0.01 mol), bis(4-fluorophenyl)sulfone (2.54 g, 0.01 mol), $K_2CO_3$ (1.65 g, 0.012 mol), DMSO (30 mL) and toluene (15 mL). The mixture was refluxed for 4 hours, and then excess toluene was distilled off. Then, the mixture was heated at 180° C. for 12 hours. The reaction mixture was poured into water (50 mL), and the polymer was separated by adding NaCl (20 g), filtered out and dried. The crude polymer was then dissolved in DMSO and precipitated in acetone. The purified polymer was filtered out, and dried in vacuo at 80° C. for two days.

The inherent viscosity of the polymer was 0.48 dL/g. It is to be noted that regarding all examples, the inherent viscosity was measured in a DMSO solution of a polymer at a polymer concentration of 0.25 g/dL at 30° C., using an Ostwald capillary viscometer.

A 20% DMF solution of the thus obtained polymer was prepared, and was applied to a glass plate, using a doctor blade with a gap size of 300 μm. The solvent was distilled off at 50° C., 120° C., and 200° C., each for one hour, to form a membrane with a thickness of about 55 μm. Then, the membrane was immersed in a 1 mol /L sulfuric acid for 24 hours, and washed with deionized water until the acid was not detected any more. In this way, an electrolyte membrane (test sample) was obtained.

It is to be noted that regarding all examples below, the measurement of methanol permittivity was determined by keeping a 10 wt. % aqueous methanol solution and deionized water, separated from each other by an electrolyte membrane (test sample) (55 μm thick) in a stainless steel vessel at 30° C., and measuring the amount of methanol seeped into the deionized water by GC/MS at a specific time interval. The methanol permittivity of this example was $2.01 \times 10^{-8}$ mL/s.cm. On the other hand, the methanol permittivity of Nafion 112 was $1.08 \times 10^{-7}$ mL/s.cm.

It is also to be noted that regarding all examples, the measurement of proton conductivity was determined by placing a test sample between platinum electrodes that are kept 1 cm apart, measuring the film resistance of the test sample by an alternate current impedance method (frequency from 100 Hz to 100 kHz), at room temperature and at a voltage of 0.3 V, and calculating the proton conductivity from the data. The proton conductivity of the membrane of this example was 0.087 S/cm. On the other hand, the proton conductivity of Nafion 112 was 0.112 S/cm.

Example 13

Figure 9:
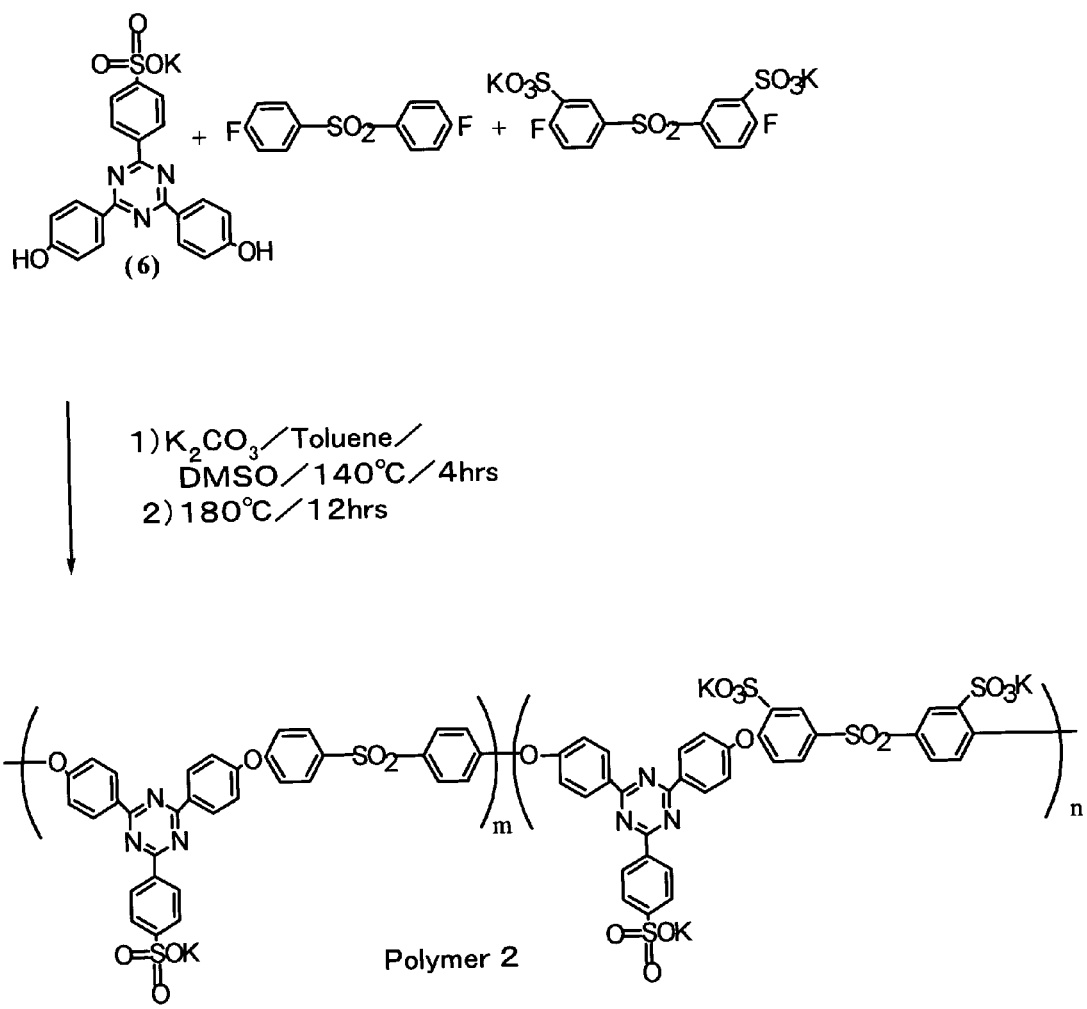
FIG. 9 shows an exemplary synthesis route of a polymer according to the present invention.

Manufacturing of Polymer 2: FIG. 9

To a 100 mL three-necked, round-bottom flask, fitted with a condenser, a Dean-Stark arm, and a nitrogen purge system were added compound 6 (4.59 g, 0.01 mol), disodium 3,3'-disulfonated-4,4'-difluorodiphenylsulfone (2.29 g, 0.005 mmol), bis(4-fluorophenyl)sulfone (1.27 g, 0.005 mol), $K_2CO_3$ (1.65 g, 0.012 mol), DMSO (30 mL) and toluene (15 mL). The mixture was refluxed for 4 hours, and excess toluene was distilled off, and the remaining mixture was heated at 180° C. for 12 hours. The reaction mixture was poured into water (50 mL), and the polymer was separated by adding NaCl (20 g), filtered out and dried. The crude polymer was then dissolved into DMSO and precipitated in acetone. The purified polymer was filtered out, and dried in vacuo at 80° C. for 2 days. The same procedure as for Example 12 was followed to form an electrolyte membrane (test sample).

The polymer had an inherent viscosity of 0.53 dL/g, and the electrolyte membrane (test sample) had a methanol permittivity of $7.02 \times 10^{-8}$ mL/s.cm, and a proton conductivity of 0.136 S/cm.

Example 14

Figure 10:
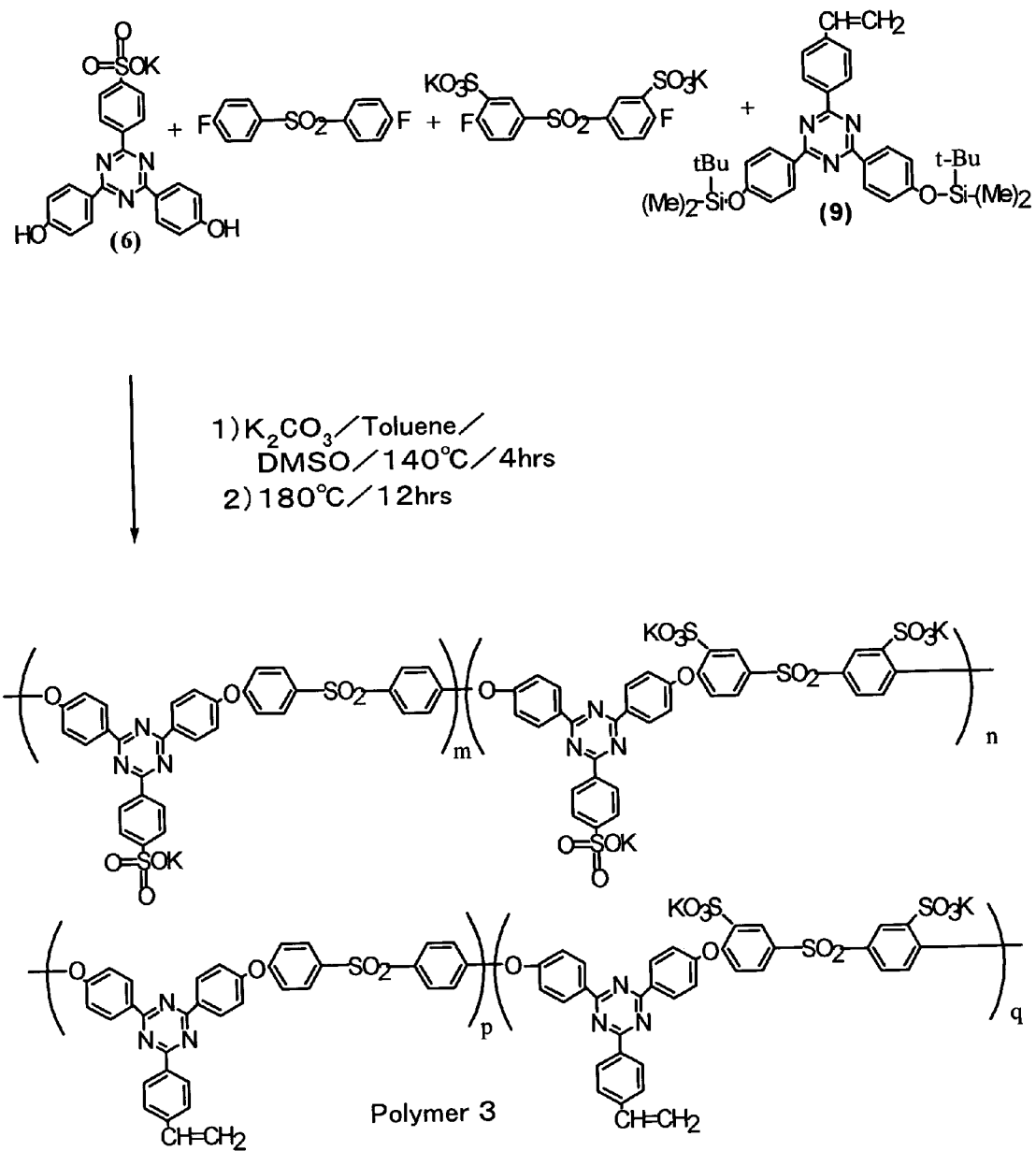
FIG. 10 shows an exemplary synthesis route of a polymer according to the present invention.

Manufacturing of Polymer 3: FIG. 10

To a 100 mL three-necked, round-bottom flask, fitted with a condenser, a Dean-Stark arm, and a nitrogen purge system were added compound 6 (3.67 g, 0.008 mol), disodium-3,3'-disulfonated-4,4'-difluorodiphenylsulfone (2.29 g, 0.005 mmol), bis(4-fluorophenyl)sulfone (1.27 g, 0.005 mol), $K_2CO_3$ (1.38 g, 0.010 mol), DMSO (30 mL) and toluene (15 mL). The mixture was refluxed for 4 hours, and excess toluene was distilled off under a reduced pressure. Then, the remaining mixture was heated at 180° C. for 12 hours. The reaction mixture was cooled, and compound 9 (1.19 g, 0.002 mol) and CsF (0.03 g, 0.00016 mol) were added. The mixture was then heated at 120° C. for 6 hour. The reaction mixture was poured into water (50 mL), and the polymer was separated by adding NaCl (20 g), filtered out and dried. The crude polymer was then dissolved in DMSO and precipitated in acetone. The purified polymer was filtered out, and dried in vacuo at 80° C. for 24 hours.

The polymer (2.0 g), divinylbenzene (0.2 g, 1.5 mmol) and 2,2'-azobisisobutyronitrile (AIBN, 5 mg, 0.03 mmol) were dissolved in 10 mL of THF/methanol (50 vol. %). The solution was degassed in a tube by a freeze-thaw procedure. The tube was sealed and shaken at 80° C. for 48 hours. The polymer was precipitated by pouring into hexane. The solid product was dried in vacuo at 80° C. for 24 hours. The same procedure as for Example 12 was followed to form an electrolyte membrane (test sample).

The electrolyte membrane (test sample) had a methanol permittivity of $4.20 \times 10^{-8}$ mL/s.cm, and a proton conductivity of 0.109 S/cm.

Example 15

Manufacturing of Polymer 4: FIG. 11

To a 100 mL three-necked, round-bottom flask, fitted with a condenser, a Dean-Stark arm, and a nitrogen purge system were added compound 12 (4.21 g, 0.01 mol), 2,2-bis(4-hydroxyphenyl)-1,1,1,3,3,3-hexafluoropropane (3.36 g, 0.01 mol), $K_2CO_3$ (1.65 g, 0.012 mol), DMSO (30 mL) and toluene (15 mL). The mixture was refluxed for 4 hours, and excess toluene was distilled off. Then, the mixture was heated at 180° C. for 12 hours. The reaction mixture was poured into water (50 mL), and the polymer was separated by adding NaCl (20 g), filtered out and dried. The crude polymer was then dissolved in DMSO and precipitated in acetone. The purified polymer was filtered out, and dried in vacuo at 80° C. for 2 days. The same procedure as for Example 12 was followed to form an electrolyte membrane (test sample).

The polymer had an inherent viscosity of 0.48 dL/g, and the electrolyte membrane (test sample) had a methanol permittivity of $3.0 \times 10^{-8}$ mL/s.cm, and a proton conductivity of 0.081 S/cm.

Example 16

Figure 12:
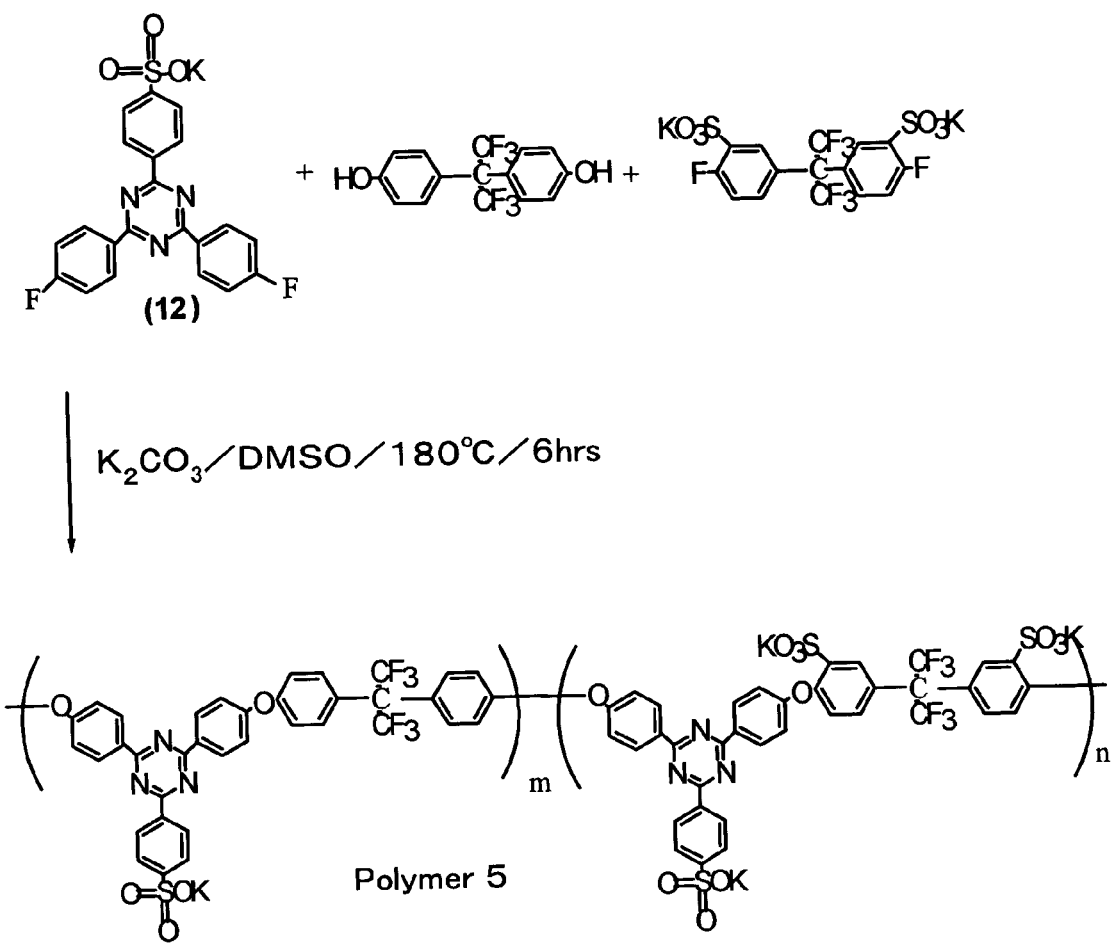
FIG. 12 shows an exemplary synthesis route of a polymer according to the present invention.

Manufacturing of Polymer 5: FIG. 12

To a 100 mL three-necked, round-bottom flask, fitted with a condenser, a Dean-Stark arm, and a nitrogen purge system, were added compound 12 (2.11 g, 0.005 mol), disodium-3, 3'-disulfonated-4,4'-difluorodiphenylsulfone (2.29 g, 0.005 mmol), 2,2-bis(4-hydroxyphenyl)-1,1,1,3,3,3-hexafluoropropane (3.36 g, 0.01 mol), $K_2CO_3$ (1.65 g, 0.012 mol), DMSO (30 mL) and toluene (15 mL). The mixture was refluxed for 4 hours, and excess toluene was distilled off. Then, the reaction mixture was heated at 180° C. for 12 hours. The reaction mixture was poured into water (50 mL), and the polymer was separated by adding NaCl (20 g), filtered out and dried. The crude polymer was then dissolved in DMSO and precipitated in acetone. The purified polymer was filtered out, and dried in vacuo at 80° C. for 2 days. The same procedure as for Example 12 was followed to form an electrolyte membrane (test sample).

The polymer had an inherent viscosity of 0.60 dL/g, and the electrolyte membrane (test sample) had a methanol permittivity of $6.13 \times 10^{-8}$ mL/s.cm, and a proton conductivity of 0.129 S/cm.

What is claimed is:

1. An electrolyte composition comprising a sulfonic acid group-containing polymer having at least one structure unit selected from the group consisting of a structure unit represented by formula (1), a structure unit represented by formula (2), a structure unit represented by formula (3), and a structure unit represented by formula (4),

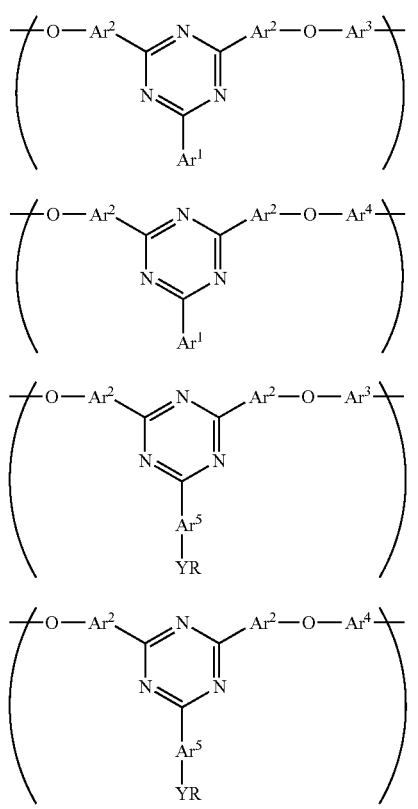

(in formulae (1)-(4), Y is, independently for each formula, O, S or a direct bond; R is, independently for each formula, a group having at least either one of an unsaturated bond and an epoxy bond; $Ar^1$ is, independently for each formula, a sulfonic acid group-containing monovalent aromatic ring that may comprise fluorine or a fluorine-containing substituent group; $Ar^2$ is, independently for each formula and from each other in each formula, a divalent aromatic ring that may comprise fluorine or a fluorine-containing substituent group; $A^3$ is, independently for each formula, a divalent group comprising an aromatic ring that may comprise fluorine or a fluorine-containing substituent group; $Ar^4$ is, independently for each formula, a divalent group comprising a sulfonic acid group-containing aromatic ring that may comprise fluorine or a fluorine-containing substituent group; and $Ar^5$ is a phenylene group that may have 1 to 4 fluorine atoms as substituents).

2. An electrolyte composition according to claim 1, wherein said sulfonic acid group-containing polymer is cross-linkable by an active energy ray irradiation treatment, a heat treatment, or a combination thereof.

3. An electrolyte composition according to claim 1, wherein said sulfonic acid group-containing polymer is a homopolymer, a random copolymer, a block copolymer, or a mixture thereof.

4. An electrolyte composition according to claim 1, wherein $Ar^1$ is, independently for each formula, a sulfonic acid group-containing phenyl group that may comprise fluorine or a fluorine-containing substituent group.

5. An electrolyte composition according to claim 1, wherein the two $A^2$'s in each formula are phenylene groups that may comprise fluorine or a fluorine-containing substituent group.

6. An electrolyte composition according to claim 1, wherein $Ar^1$ comprises one or two sulfonic acid groups.

7. An electrolyte composition according to claim 1, wherein Y is a direct bond, and R is a group selected from the group consisting of $CH=CH_2, CH_2CH=CH_2$ and $CF=CF_2$.

8. An electrolyte composition according to claim 1, wherein at least either one of $Ar^3$ and $Ar^4$ has a structure unit selected from the group consisting of a phenylene sulfone structure unit, a phenylene sulfoxide structure unit, a phenylene ketone structure unit, a phenylene ether structure unit, a benzoxazole structure unit, a benzothiazole structure unit and a triphenyl phosphine oxide structure unit.

9. An electrolyte composition according to claim 1, wherein the structure unit represented by formula (1) is obtained by reacting a compound represented by formula (5) and a compound represented by formula (6),

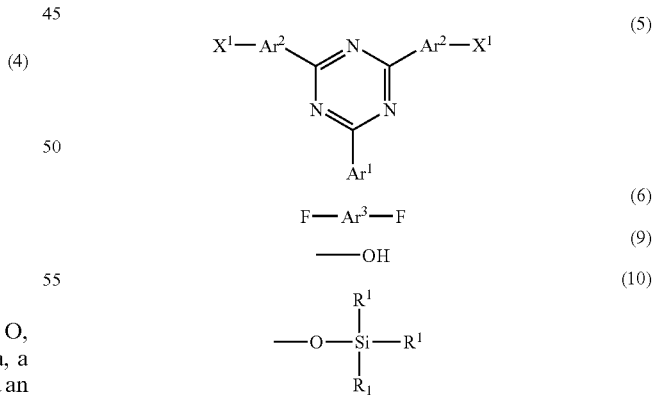

(in formulae (5) and (6), $X^1$ is, independently from each other, a group represented by formula (9) or (10); in formula (10), $R^1$ is, independently from each other, an alkyl group that may be branched; the other symbols have the same meanings as in formulae (1) to (4); and the sulfonic acid group in $Ar^1$ may be a salt of an alkali metal or an alkaline earth metal).

10. An electrolyte composition according to claim 1, wherein the structure unit represented by formula (2) is obtained by reacting a compound represented by formula (5) and a compound represented by formula (7),

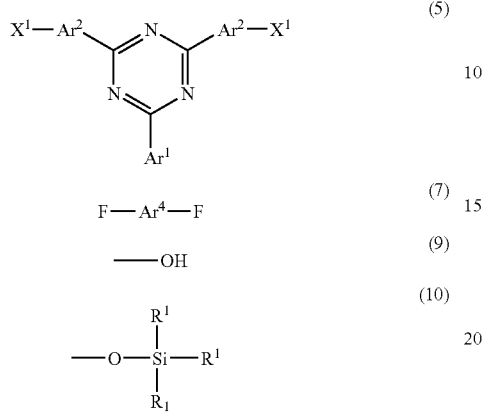

(in formulae (5) and (7), $X^1$ is, independently from each other, a group represented by formula (9) or (in (10); in formula (10), $R^1$ is, independently from each other, an alkyl group that may be branched; the other symbols have the same meanings as in formulae (1) to (4); and the sulfonic acid group in $Ar^1$ and $Ar^4$ may be a salt of an alkali metal or an alkaline earth metal).

11. An electrolyte composition according to claim 1, wherein the structure unit represented by formula (3) is obtained by reacting a compound represented by formula (8) and a compound represented by formula (6),

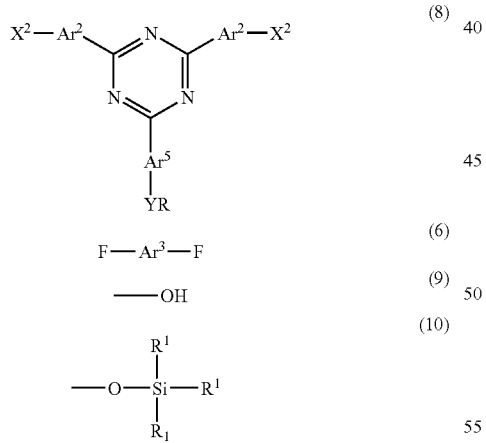

(in formulae (8) and (6), $X^2$ is, independently from each other, a group represented by formula (9) or (10); in formula (10), $R^1$ is, independently from each other, an alkyl group that may be branched; and the other symbols have the same meanings as in formulae (1) to (4)).

12. An electrolyte composition according to claim 1, wherein the structure unit represented by formula (4) is obtained by reacting a compound represented by formula (8) and a compound represented by formula (7),

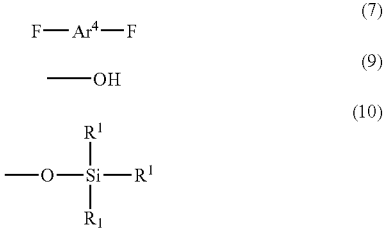

(in formulae (8) and (7), $X^2$ is, independently from each other, a group represented by formula (9) or (10); in formula (10), $R^1$ is, independently from each other, an alkyl group that may be branched; the other symbols have the same meanings as in formulae (1) to (4); and the sulfonic acid group in $Ar^4$ may be a salt of an alkali metal or an alkaline earth metal).

13. An electrolyte composition according to claim 1, wherein said sulfonic acid group-containing polymer has a number-average molecular weight (Mn) of 5,000 to 10,000,000.

14. An electrolyte composition obtained by subjecting the electrolyte composition according to claim 1, to an active energy ray irradiation treatment, a heat treatment, or a combination thereof.

15. A solid electrolyte membrane comprising an electrolyte composition according to claim 1.

16. A solid electrolyte membrane comprising an electrolyte composition according to claim 14.

17. A solid electrolyte membrane obtained by subjecting the electrolyte composition according to claim 1, to an active energy ray irradiation treatment, a heat treatment, or a combination thereof.

18. A solid polymer fuel cell using a solid electrolyte membrane according to claim 15.

19. A solid polymer fuel cell using a solid electrolyte membrane according to claim 16.

20. A solid polymer fuel cell using a solid electrolyte membrane according to claim 17.

21. A method for manufacturing a solid electrolyte membrane, wherein the electrolyte composition according to claim 1, comprises an organic solvent, said electrolyte composition comprising the organic solvent is applied to a substrate, and said solvent is removed thereafter.

22. A method for manufacturing a solid electrolyte membrane according to claim 21, wherein after the removal of said organic solvent, an active energy ray irradiation treatment, a heat treatment, or a combination thereof, is performed.

23. A method for manufacturing a solid electrolyte membrane according to claim 21, wherein
   a hot rolling treatment is performed after the removal of said organic solvent.

24. A method for manufacturing a solid electrolyte membrane according to claim 22, wherein
   a hot rolling treatment is performed after the active energy ray irradiation treatment, a heat treatment, or a combination thereof.

25. A solid polymer fuel cell using a solid electrolyte membrane manufactured by the method according to claim 21.

26. A solid polymer fuel cell using a solid electrolyte membrane manufactured by the method according to one of claims 22 to 24.

* * * * *